US00PP23174P3

(12) United States Plant Patent
Carruth

(10) Patent No.: US PP23,174 P3
(45) Date of Patent: Nov. 13, 2012

(54) FLORIBUNDA ROSE PLANT NAMED 'WEKPLALAJARO'

(50) Latin Name: *Rosa hybrida*
Varietal Denomination: WEKplalajaro

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 76 days.

(21) Appl. No.: 12/927,799

(22) Filed: Nov. 24, 2010

(65) Prior Publication Data

US 2012/0131705 P1 May 24, 2012

(51) Int. Cl.
*A01H 5/00* (2006.01)

(52) U.S. Cl. ..... Plt./141

(58) Field of Classification Search ..... Plt./141, Plt./143, 147, 146

See application file for complete search history.

*Primary Examiner* — June Wu

(74) *Attorney, Agent, or Firm* — McKee, Voorhees & Sease, P.L.C.

(57) ABSTRACT

A new variety of Floribunda rose suitable for garden decoration, having flowers of salmon blend blushing scarlet coloration.

1 Drawing Sheet

Classification: The present invention relates to a new *Rosa hybrida* plant.

Variety denomination: The new plant has the varietal denomination 'WEKplalajaro'.

BACKGROUND OF THE INVENTION

This invention relates to a new and distinct variety of Floribunda Rose. It has an undisseminated seedling of my creation as its seed parent with the following genetic origin (Playboy×Lagerfeld) and as its pollen parent the variety known as 'WEKausboy' (U.S. Plant Pat. No. 20,742).

SUMMARY OF THE INVENTION

Among the features which distinguish the new variety from other presently available and commercial rose cultivars known to the inventor are the following combinations of characteristics: its numerous stipitate glands on the peduncle and on the surface of the bud, its red suffusion on the inner surface of the sepal that appears as the flower ages, its many small prickles on the major stems, branches and new shoots and its complex salmon blend blushing scarlet flower coloration. The plant has an upright somewhat spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKplalajaro' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling of my creation by the following combination of characteristics: whereas 'WEKplalajaro' bears double flowers (about 22 to 31 petals) of salmon blend blushing scarlet coloration, the undisseminated seedling bears semi-double flowers of warm apricot gold coloration with significantly lesser petalage (about 13 to 18 petals).

The new variety may be distinguished from its pollen parent, 'WEKausboy' by the following combination of characteristics: whereas 'WEKplalajaro' bears large size flowers (about 9.8 to about 12.8 cm. in diameter) with double petalage (about 22 to 31 petals), 'WEKausboy' bears significantly smaller flowers (about 8 to about 10 cm. in diameter) with lesser petalage (about 12 to 15 petals). The new variety bears flowers of salmon blend blushing scarlet coloration, whereas the pollen parent bears flowers of multicolor yellow, pink and red coloration.

COMPARISON WITH THE CLOSEST COMMERCIALLY AVAILABLE CULTIVAR

The new variety may be distinguished from its closest commercially available cultivar, 'MEImonblan' (U.S. Plant Pat. No. 12,579) by the following combination of characteristics: whereas 'WEKplalajaro' bears large size flowers (about 9.8 to about 12.8 cm. in diameter) of salmon blend blushing scarlet coloration, 'MEImonblan' bears significantly smaller flowers (approximately 9 to 10 cm. on average in diameter) of attractive marigold orange coloration. The new variety has an upright somewhat spreading medium height to somewhat tall growing habit (about 140 to about 160 cm. in height, whereas the closest commercially available cultivar has a significantly shorter bushy growing habit (approximately 65 to 75 cm. on average in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong medium to somewhat long stems (about 26 to about 72 cm.). Outdoors, the plant blooms abundantly and nearly continuously during the growing season. The flowers have a moderate citrus-like to apple-like fragrance.

BUD

The peduncle is about 5.7 to about 11.1 cm. in length, of average to somewhat heavy caliper (about 0.3 to about 0.4 cm. in diameter), and usually erect. It is rough, with numerous stipitate glands and few hairs. Peduncle color is between 146B and 146D often heavily suffused, especially on the side exposed to the sun, with between 187B and 187A.

Before the calyx breaks, the bud is about 1.3 to about 1.9 cm. in diameter at the widest point, about 1.7 to about 2.4 cm. in length, and pointed to somewhat ovoid in shape. The surface of the bud bears between 5 to 7 foliaceous appendages with numerous stipitate glands and some hairs, usually with stout much cut foliaceous parts extending beyond the tip of the bud about ¾ or more of its length. Bud color is between 146B and 146C often heavily suffused, especially on the side exposed to the sun, with between 187B and 187A.

The sepals are about 3.1 to about 6.6 cm. in length and about 0.9 to about 1.1 cm. in width at the widest point. The outer surface color of the sepal is between 146B and 146C often heavily suffused, especially on the side exposed to the sun, with between 187B and 187A. The inner surface color of the sepal is near 146B broadly bordered by near 137B. After the sepals open, the inner surface color is often heavily suffused, especially on the area exposed to the sun, with between 187A and 187B. The inner surface of the sepal is covered with fine wooly tomentum; sepal margins are lined with numerous stipitate glands and some hairs.

The receptacle of the flower is of moderately short length (about 0.4 to about 0.6 cm.) and somewhat thin in caliper (about 0.7 to about 0.9 cm. in diameter). The receptacle is urn-shaped in form. Its surface is very smooth with some hairs and with somewhat thin fleshy walls. The receptacle color is between 144A and 146B.

As the petals open (after the calyx breaks), the bud is about 2.1 to about 2.7 cm. in diameter at the widest point, about 2.5 to about 3.6 cm. in length, and ovoid in form. The color of the under surfaces of the newly opened petals is between 53B and 58B often heavily suffused on the outermost petals with between 187A and 187B. At the point where the petal attaches, there is a large zone of between 154C and 1C. The color at the base of the upper surfaces of the newly opened petals is between 11C and 9D gradually suffusing toward the petal edge with near 31C sometimes lightly blushed with between 53C and 53B. At the point where the petal attaches, there is a moderately small zone of between 3C and 4B.

BLOOM

When fully open, the bloom ranges from about 9.8 to about 12.8 cm. in diameter. Petalage is double with about 22 to 31 petals and about 1 to 4 petaloids irregularly arranged. When partially open, the bloom form is moderately high centered to somewhat cupped, and the petals are loosely spiraled to cupped with petal edges moderately reflexed outward. When fully open, the bloom form is more cupped, and the petals are loosely cupped to undulated with petal edges moderately reflexed outward and inward.

PETALS

The substance of the petals is somewhat heavy and of moderately thin thickness, with upper surfaces moderately satiny and under surfaces somewhat satiny to shiny. The petals are about 3.9 to about 6.3 cm. in length and about 4.3 to about 6.7 cm. in width at the widest point. Petal margins are entire.

The outer petals are nearly round to somewhat obovate in shape with rounded apices.

The inner petals are moderately obovate in shape with rounded apices.

Petaloids are about 1.0 to about 4.3 cm. in length and about 0.6 to about 4.8 cm. in width at the widest point. Petaloids are irregularly shaped somewhat obovate to subulate with rounded to somewhat lobed apices.

NEWLY OPENED FLOWER

The under surface color of the outer petals is between 58B and 53D often heavily suffused with between 187B and 53A. At the point where the petal attaches, there is a large zone of between 14C and 13C. The color at the base of the upper surfaces of the outer petals is between 12A and 15A gradually suffusing with between 23C and 24D often heavily blushed with between 53C and 45A to as dark as between 60A and 46A. There is no visible change in coloration at the point where the petal attaches.

The under surface color of the intermediate petals is between 58B and 53D often moderately suffused with between 187B and 53A. At the point where the petal attaches, there is a large zone of between 14C and 13C. The color at the base of the upper surfaces of the intermediate petals is between 12A and 15A gradually suffusing to between 23C and 24D often moderately blushed with between 53D and 37A to as dark as between 60A and 46A. There is no visible change in coloration at the point where the petal attaches.

The color at the base of the under surfaces of the inner petals is between 14C and 13C gradually suffusing toward the petal edge with between 20B and 19A often lightly suffused with near 60A giving a general tonality of between 53D and 58B. There is no visible change in coloration at the point where the petal attaches.

The color at the base of the upper surfaces of the inner petals is between 12A and 15A gradually suffusing to between 23B and 24D often lightly blushed with between 53D and 37A. There is no visible change in coloration at the point where the petal attaches.

The under and upper surface colors of the petaloids are similar in coloration to the upper and under surfaces of the inner petals.

The general tonality of the newly opened flower is between 12A and 15A at the base gradually suffusing with between 23B and 24D often blushed with between 53D and 37A to as dark as between 60A and 46A.

THREE-DAY-OLD FLOWER

The under surface color of the outer petals is between 58B and 57C often heavily blushed with between 187B and 60A. At the point where the petal attaches, there is a large zone of between 8D and 10D. The color at the base of the upper surfaces of the outer petals is near 8B gradually suffusing to between 29D and 27B often heavily blushed with between 58B and 57A to as dark as between 53C and 53A. There is no visible change in coloration at the point where the petal attaches.

The color at the base of the under surfaces of the intermediate and inner petals is between 10C and 8C gradually suffusing toward the petal edge with between 29C and 28D often moderately blushed with near 60A giving a general tonality of between 61D and 55A. There is no visible change in coloration at the point where the petal attaches.

The color at the base of the upper surfaces of the intermediate and inner petals is near 8B gradually suffusing to between 29D and 27B often moderately blushed with between 58B and 57A to as dark as between 53C and 53A. There is no visible change in coloration at the point where the petal attaches.

The under and upper surface colors of the petaloids are similar in coloration to the upper and under surfaces of the intermediate and inner petals.

The general tonality of the three-day-old flower is near 8B at the base gradually suffusing with between 29D and 27B often moderately blushed with between 58B and 57A to as dark as between 53C and 53A.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are of medium to somewhat long length (about 0.4 to about 1.3 cm.) most with anthers. Filaments are between 13B and 14B in color sometimes lightly suffused with near 53B. The anthers are somewhat small for the class and all open approximately at the same time. Anther color when immature is near 21B on the external part and near 10C on the internal part. Anther color at maturity is near 163B on the external part and near 200B on the internal part. Pollen is moderately abundant and between 16D and 18B in color.

FEMALE REPRODUCTIVE ORGANS

Pistils vary in number (average about 125). The styles are moderately uneven, somewhat long in length (about 0.6 to about 0.9 cm.), average in caliper and loosely separated to somewhat columnar. Stigma color is between 21D and 22D. Style color is between 1D and 154D usually heavily suffused with between 53A and 60A. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 7.1 to about 13.2 cm. in length and about 5.5 to about 11.5 cm. in width at the widest point, moderately leathery in texture, and glossy in finish on the upper side and somewhat semi-glossy to matte in finish on the under side. The terminal leaflets are about 3.3 to about 7.2 cm. in length and about 2.8 to about 5.2 cm. in width at the widest point, shaped ovate with acute apices and rounded bases. Their margins are usually simply serrate.

The upper surface color of the mature leaf is between 139A and 147A. The under surface color of the mature leaf is between 147B and 146A. The upper surface color of the young leaf is between 137A and 146C, often heavily suffused with between 187A and 187B. The under surface color of the young leaf is between 146B and 146C, often heavily suffused with between 187B and 187A.

The rachis is average in caliper and rough. The upper side is deeply grooved with some hairs and few stipitate glands on the edges of the grooves. The under side of the rachis is rough with some hairs and stipitate glands and few small prickles. The rachis color is near 146D on the under side and near 146C on the upper side often heavily suffused, especially on the young leaf with between 187A and 187B.

The stipules are about 1.2 to about 1.6 cm. in length and moderately wide (about 0.4 to about 0.6 cm.) with somewhat short straight points that usually turn out at an angle of more than 45 degrees. The under and upper surface color of the stipule is between 137C and 146A often moderately suffused, especially on the young leaf with between 187B and 187C.

The petiole is average in caliper and rough. The upper side is deeply grooved with some hairs and few stipitate glands on the edges of the grooves. The under side of the petiole is rough with some hairs and stipitate glands and few small prickles. The petiole is about 0.8 to about 1.4 cm. in length and about 0.1 to about 0.15 cm in width at the widest point. The petiole color is near 146D on the under side and near 146C on the upper side often heavily suffused, especially on the young leaf with between 187A and 187B.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright somewhat spreading medium height to somewhat tall growing habit (about 140 to about 160 cm. in height and about 54 to about 72 cm. spread at the widest point), with full branching. It displays vigorous growth and the canes are of medium caliper for the class (about 1.1 to about 1.8 cm. in width at the widest point).

The color of the major stems is between 152A and 152B. They bear some large prickles that are about 0.7 to about 0.9 cm. in length. The large prickles are angled moderately downward with a somewhat short broad oval base; prickle color is between 164A and 166B sometimes lightly suffused with between 201A and 201B. The major stem bears many small prickles of similar coloration. The small prickles are almost straight to angled slightly downward with a somewhat short broad oval base.

The color of the branches is between 146A and 137C. They bear some large prickles which are of similar size and shape to the large prickles on the major stems; prickle color is between 164A and 166C. The branches bear many small prickles of similar shape and coloration.

The color of the new shoots is between 146B and 146C often heavily suffused with between 187B and 187A. They bear some large prickles which are of similar size and shape to the large prickles on the major stems; prickle color is near 152B often heavily suffused with between 187A and 187B. The shoots bear many small prickles of similar shape and coloration.

I claim:

1. A new and distinct Floribunda rose plant of the variety substantially as described and illustrated herein.

* * * * *

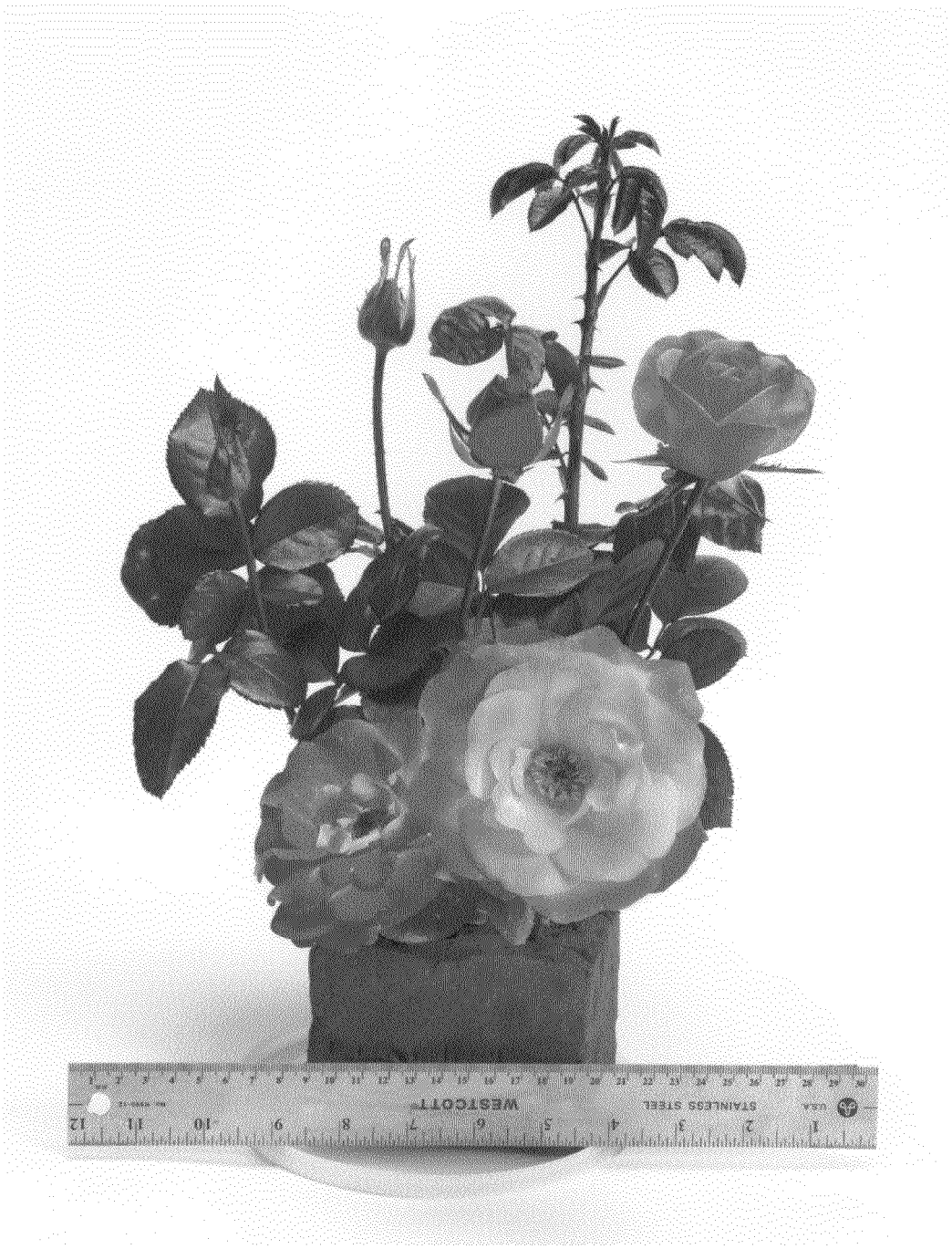
WESTCOTT
STAINLESS STEEL